United States Patent
Presura et al.

(10) Patent No.: US 10,856,738 B2
(45) Date of Patent: Dec. 8, 2020

(54) DEVICE FOR MEASURING A PHYSIOLOGICAL PARAMETER OF A USER

(71) Applicant: KONINKLIJKE PHILIPS N.V., Eindhoven (NL)

(72) Inventors: Cristian Nicolae Presura, Veldhoven (NL); Pieter Geert Van Engen, Nuenen (NL); Alphonsus Tarcisius Jozef Maria Schipper, Stramproy (NL); Koen Geenen, Gilze (NL); Gerardus Franciscus Cornelis Maria Lijten, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/397,221

(22) PCT Filed: Dec. 11, 2013

(86) PCT No.: PCT/IB2013/060807
§ 371 (c)(1),
(2) Date: Oct. 27, 2014

(87) PCT Pub. No.: WO2014/091424
PCT Pub. Date: Jun. 19, 2014

(65) Prior Publication Data
US 2015/0282712 A1 Oct. 8, 2015

Related U.S. Application Data

(60) Provisional application No. 61/737,136, filed on Dec. 14, 2012.

(51) Int. Cl.
*A61B 5/00* (2006.01)
*A61B 5/024* (2006.01)
(Continued)

(52) U.S. Cl.
CPC .......... *A61B 5/0059* (2013.01); *A61B 5/0205* (2013.01); *A61B 5/02427* (2013.01);
(Continued)

(58) Field of Classification Search
CPC ... A61B 5/6833; A61B 5/6824; A61B 5/6831; A61B 5/02427; A61B 5/02416;
(Continued)

(56) References Cited

U.S. PATENT DOCUMENTS

| 5,078,136 A | 1/1992 | Stone et al. |
| 5,638,818 A * | 6/1997 | Diab .................. A61B 5/02427 356/41 |

(Continued)

FOREIGN PATENT DOCUMENTS

| DE | 102008030956 A1 | 4/2009 |
| JP | 0518503 U | 3/1993 |

(Continued)

OTHER PUBLICATIONS

Chirag J. Pujary: "Investigation of Photodetector Optimization in Reducing Power Consumption by a Noninvasive Pulse Oximeter Sensor"; Thesis, Worcester Polytechnic Institute, Jan. 2004, 133 Pages.

*Primary Examiner* — Carl H Layno
*Assistant Examiner* — Jessandra F Hough

(57) ABSTRACT

A device for measuring a physiological parameter of a user carrying the device that includes a sensor having at least two sensor elements for detecting a sensor signal, a carrier configured to carry the sensor, and electrical contacts of the sensor elements that lead on, into or through the carrier. One or more frames carried by the carrier are formed around the sensor and/or the individual sensor elements, and an insulator material is filled between the one or more frames and the sensor and/or the sensor elements surrounded by a
(Continued)

respective frame without covering a top surface of a respective sensor element facing away from the carrier.

20 Claims, 3 Drawing Sheets

(51) Int. Cl.
    *A61B 5/0205*     (2006.01)
    *A61B 5/053*     (2006.01)
    *A61B 5/0245*     (2006.01)

(52) U.S. Cl.
    CPC .......... *A61B 5/6824* (2013.01); *A61B 5/6831* (2013.01); *A61B 5/6833* (2013.01); *A61B 5/72* (2013.01); *A61B 5/0245* (2013.01); *A61B 5/02438* (2013.01); *A61B 5/02444* (2013.01); *A61B 5/0531* (2013.01); *A61B 5/681* (2013.01); *A61B 2560/0412* (2013.01); *A61B 2562/0233* (2013.01); *A61B 2562/12* (2013.01); *Y10T 29/49171* (2015.01)

(58) Field of Classification Search
    CPC ... A61B 5/02438; A61B 5/024; A61B 5/1455; A61B 5/1451; A61B 2562/0233; A61B 2562/12; A61B 2560/04; A61B 2560/0462; A61B 2562/168; A61B 5/02; A61B 5/14552; A61B 5/0059; A61B 5/0205; A61B 5/72; A61B 5/02444; A61B 5/0245; A61B 5/0531; A61B 5/681; A61B 2560/0412; A61B 2562/16; Y10T 29/49171; Y10T 29/49158
    USPC .......................................................... 600/323
    See application file for complete search history.

(56) References Cited

U.S. PATENT DOCUMENTS

| | | |
|---|---|---|
| 5,807,267 A | 9/1998 | Bryars et al. |
| 7,869,849 B2 * | 1/2011 | Ollerdessen ....... A61B 5/14552 |
| | | 600/323 |
| 2005/0075553 A1 | 4/2005 | Sakai et al. |
| 2007/0123756 A1 * | 5/2007 | Kitajima ............ A61B 5/14552 |
| | | 600/300 |
| 2007/0276270 A1 * | 11/2007 | Tran .................... A61B 5/0022 |
| | | 600/508 |
| 2008/0076982 A1 | 3/2008 | Ollerdessen et al. |
| 2009/0048526 A1 | 2/2009 | Kpenv |
| 2009/0182208 A1 * | 7/2009 | Cho .................... A61B 5/0059 |
| | | 600/310 |
| 2011/0186736 A1 * | 8/2011 | Yao .................... H01L 31/0203 |
| | | 250/338.4 |
| 2012/0130260 A1 | 5/2012 | Borgos et al. |
| 2014/0278229 A1 * | 9/2014 | Hong .................... A63B 71/06 |
| | | 702/160 |

FOREIGN PATENT DOCUMENTS

| | | | |
|---|---|---|---|
| JP | 2003325465 A | 11/2003 | |
| JP | 2005040261 A | 2/2005 | |
| JP | 2008272085 A | 11/2008 | |
| RU | 2195168 C2 | 12/2002 | |
| RU | 2378982 C2 | 1/2010 | |
| WO | 2011051888 A2 | 5/2011 | |
| WO | WO2011/051888 | * 5/2011 | ............... A61B 5/00 |
| WO | 2011076886 | 6/2011 | |

* cited by examiner

DEVICE FOR MEASURING A PHYSIOLOGICAL PARAMETER OF A USER

CROSS-REFERENCE TO PRIOR APPLICATIONS

This application is the U.S. National Phase application under 35 U.S.C. § 371 of International Application No. PCT/IB2013/060807, filed on Dec. 11, 2013, which claims the benefit of U.S. Provisional Patent Application No. 61/737,136, filed on Dec. 14, 2012. These applications are hereby incorporated by reference herein.

FIELD OF THE INVENTION

The present invention relates to a device for measuring a physiological parameter of a user carrying said device. Further, the present invention relates to a method of manufacturing a device for measuring a physiological parameter.

BACKGROUND OF THE INVENTION

Heart rate monitors have been used in the field of leisure and sport for some years already. There are many makes of these devices. Typical devices have the form of a (e.g. ECG) chestband or wristband, e.g. including a sensor of the optical type that measures on the arm. Such a heart rate monitor is e.g. known from US 2009/048526.

US 2009/048526 discloses a monitoring apparatus for monitoring a user's heart, the apparatus comprising several sensors for measuring changes in an electrical parameter of a user's arm, from which changes in an electrocardiogram, heart rate and/or heart rate variation of the user's heart are determinable. The apparatus further comprises a data processor for determining the electrocardiogram, the heart rate and/or heart rate variation from the changes in the electrical parameter; and an output device for making knowable to the user the electrocardiogram, heart rate and/or heart rate variation. Only a single wristband, particularly a wrist watch, is used having all the means to monitor the user's heart, without using for example a chest band. Herein, the single wristband is at least provided with the at least one sensor and particularly also comprises the data processor, and more particularly also comprises the output device.

Other wearable measurement devices use conductivity sensors for measuring the conductivity of the skin to make use of the known fact that skin conductance of a user is related with the level of arousal of the user.

For protection of the electrical components, by which the sensor is generally connected to other electrical components, such as a driver, processor, controller and/or power source, the electrical contacts of the sensor are generally covered with an insulator material, such as epoxy resin. However, it should be avoided to cover the top surface of the sensor elements, in particular of the light emitting diodes and preferably also of the photo diode in case of an optical sensor, because otherwise this bears the risk that the covered sensor element looses grip to the user's skin which may reduce the signal quality or even the ability to measure a useful signal at all.

SUMMARY OF THE INVENTION

It is an object of the present invention to provide a device for measuring a physiological parameter of a user carrying said device in which the internal electrical contacts are safely protected without impeding the performance of the device. It is a further object of the present invention to provide a simple method of manufacturing such a device.

In a first aspect of the present invention a device for measuring a physiological parameter of a user carrying said device is presented that comprises:
  a sensor comprising at least two sensor elements for detecting a sensor signal,
  a carrier carrying said sensor, wherein electrical contacts of said sensor elements lead on, into or through said carrier,
  one or more frames carried by said carrier and formed around said sensor and/or said individual sensor elements,
  a insulator material filled between said one or more frames and the sensor and/or the sensor elements surrounded by the respective frame without covering the top surface of the respective sensor element facing away from the carrier.

In a further aspect of the present invention a method of manufacturing such a device is presented that comprises:
  arranging a sensor comprising at least two sensor elements for detecting a sensor signal on a carrier for carrying said sensor,
  forming electrical contacts of said sensor elements on, into or through said carrier,
  forming one or more frames on said carrier around said sensor and/or said individual sensor elements,
  filling insulator material between said one or more frames and the sensor and/or the sensor elements surrounded by the respective frame without covering the top surface of the respective sensor element facing away from the carrier.

Preferred embodiments of the invention are defined in the dependent claims. It shall be understood that the claimed method has similar and/or identical preferred embodiments as the claimed device and as defined in the dependent claims.

The present invention is based on the idea to use one or more frames around the complete sensor or around the individual sensor elements, made in such a way as to preserve the performance of the sensor. For instance, at least one of these frames helps to prevent shifting of the sensor across the skin. Moreover, dependent on the kind of sensor, one or more frames may additionally help to separate signals emitted by one or more sensor elements and/or signals received by one or more sensor elements. The one or more frames particularly serve to confine the insulator material when it is poured over the electrical contacts between the frame and the respective sensor element so that it does not spill out and negatively impact the correct functioning of the device.

Generally, the particular kind of sensor that measures one or more physiological parameters (e.g. heart rate, blood pressure, breathing rate, skin conductivity, skin humidity, etc.) is not essential for the present invention. In a preferred embodiment said sensor is an optical sensor comprising at least one light emitting element, in particular an LED, for emitting light to the user's skin and at least one light receiving element, in particular a photo detector, for receiving light reflected from the user's skin. Such an embodiment may e.g. be used for heart rate monitoring. In such an embodiment the one or more frames serve to prevent direct light emitted from the light emitting element from entering the light receiving element.

Preferably, said at least one light receiving element, in particular each light receiving element, is surrounded by a separate receiver frame having a height from the carrier that is larger than the distance between the carrier and the top surface of the respective light receiving element surrounded by said receiver frame. It has particularly been found that this height difference is advantageous in such an optical sensor to avoid light interference with direct light. In addition, because the receiver will push into the user's skin, the mechanical contact will increase between the skin and the sensor. Another advantage is that the light that travels from the LED to the light receiver will be forced to pass through deeper areas of the skin and less shallow areas. This will increase the robustness of the optical signal.

In a practical implementation of such a device with an optical sensor the height difference between the top edge of the receiver frame and the top surface of the respective light receiving element surrounded by said receiver frame is in the range from 0 mm to 0.5 mm, in particular in the range from 0.1 mm to 0.2 mm.

Further, it is preferred that said at least one light emitting element, in particular each light emitting element, is surrounded by an emitter frame having a height from the carrier that is smaller than or equal to the distance between the carrier and the top surface of the respective light emitting element surrounded by said emitter frame. It has particularly been found that this height difference is advantageous in such an optical sensor to optimize the optical contact between the light emitting element and the user's skin. Because the frame is lower, the surface of the light emitting element will push optimally into the user's skin, avoiding air gaps that may form and that lead to larger artefacts in the optical signal.

In a practical implementation of such a device with an optical sensor the height difference between the top edge of the emitter frame and the top surface of the respective light emitting element surrounded by said emitter frame is in the range from 0.1 mm to 0.8 mm, in particular in the range from 0.2 mm to 0.5 mm. If both frames coincide at the location between the light receiving and light emitting elements, the frame will be higher than the light emitting element itself, but only at that side.

Preferably, the distance between the carrier and the top surface of said at least one light emitting element is equal to or smaller than the distance between the carrier and the top surface of said least one light receiving element. This ensures that the light receiving element(s) is (are) pushed further into the user's skin enabling a better contact, preventing movements of the whole device and ensuring better collection of light scattered into the skin.

In another implementation there may be only one wall between the detector and the at least one light emitting element for practical reasons, e.g. in cases where the detector and at least one light emitting element are close. If that is the case the frame walls of both the frames of respectively the light receiving and light emitting elements coincide. This means that the frame wall of the light emitting element will be higher than the surface of the light emitting element itself, but only at the side where the light receiving element is situated. The remainder of the frame of the light emitting element will be lower than the surface of the element itself, in accordance with above mentioned requirements.

According to an alternative embodiment said sensor is an electrical sensor comprising two skin conductance electrodes for contacting the user's skin and measuring conductivity the user's skin. This embodiment may, for instance, be used for stress monitoring.

Generally, the device may output its sensor signals to another device, e.g. to a computer, where the sensor signals are processed. Alternatively, as preferred in an embodiment, the device further comprises additional components, such as a processor for processing said sensor signal, in particular for determining the user's heart rate when an optical sensor is used.

Said additional components are preferably arranged on said carrier on a different surface than said sensor. This prevents said additional components from impeding good contact between the sensor elements and the skin.

In another implementation said additional components are mounted on a different carrier than the sensor components for reasons of manufacturability. In that case the carrier with sensor components is preferably mounted directly on the carrier with said other components.

Generally, any kind of insulator material can be used. Preferably, said insulator material is epoxy resin.

For fixation or attaching the device to the user's skin, the device preferably further comprises a fixation element for fixing the device to the user's skin. Said fixation element may e.g. be a wristband, an adhesive strip, a band aid or a strap.

According to another aspect of the present invention a device for measuring a physiological parameter of a user carrying said device is presented, said device comprising:
  a sensor comprising at least two sensor elements for detecting a sensor signal, wherein said sensor is an optical sensor comprising at least one light emitting element, in particular an LED, for emitting light to the user's skin and at least one light receiving element, in particular a photo detector, for receiving light reflected from the user's skin, and
  a carrier carrying said sensor,
wherein the distance between the carrier and the top surface of said least one light emitting element is equal to or smaller than the distance between the carrier and the top surface of said least one light receiving element.

Preferably, in a further improvement of said aspect the space between the at least one light emitting element and the at least one light receiving element is filled with light absorbing (e.g. black) material (e.g. epoxy resin) to avoid that light can directly enter from the at least one light emitting element to the at least one light receiving element. Further, in an improvement a single frame is provided between a light receiving element and a light emitting element. Then, only on those sides that are not facing the light receiving element the distance between the carrier and the top surface of said least one light emitting element is equal to or smaller than the distance between the carrier and the top surface of said least one light receiving element.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
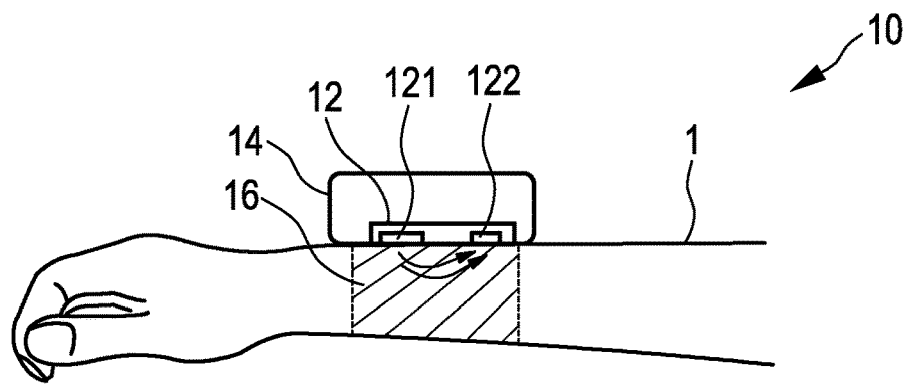
FIG. 1 shows a cross section through a known heart rate monitoring device.

FIG. 1 shows a cross section through a known device 10 for measuring a physiological parameter of a user 1 carrying said device (FIG. 1 only shows the user's arm). It comprises a sensor 12 for measuring at least one physiological parameter of the user 1 and a case 14 housing said sensor 12. The case is held on the user's arm by a fixation 16, e.g. a wristband.

The sensor 12 comprises, in this embodiment, two sensor elements 121, 122 and may be a heart rate monitoring sensor for measuring or monitoring the heart rate. But generally, the particular kind of sensor that measures one or more physiological parameters (e.g. heart rate, blood pressure, breathing rate, skin conductivity, skin humidity, etc.) is not essential for the present invention.

The case 14 may be a housing, e.g. of the type of a wristband, a wristwatch or monitoring device as used e.g. in sports. The particular kind and form of case 14 is also not essential for the present invention, but mainly serves to hold the sensor 12 at a desired position with respect to the user 1 and to optionally house further elements like a battery, a processing unit, a display, a user interface, etc.

In this embodiment the device 10 is implemented as a heart rate monitoring device 10 for monitoring the user's heart rate, and the sensor 12 is an optical sensor comprising a light emitting element 121 and a light receiving element 122. The principle of optical heart rate monitors relies on a light source 121 (usually a LED) that shines light inside the skin. Light is scattered in the skin, where it is absorbed more or less by blood. The light exits the skin and it is captured by light receiving element 122 (usually a photodiode). The amount of the signal on the light receiving element 122 is an indication of the blood volume. When the heart pulsates the blood volume in the skin changes and thus the signal on the light receiving element 122 changes as well. The light receiving element 122 measures thus directly the pulse in the skin and thus the heart rate. By counting the number of pulses per unit time, e.g. per 10 seconds, the number the heart beats per minute (i.e. the heart rate) is obtained.

Figure 2:
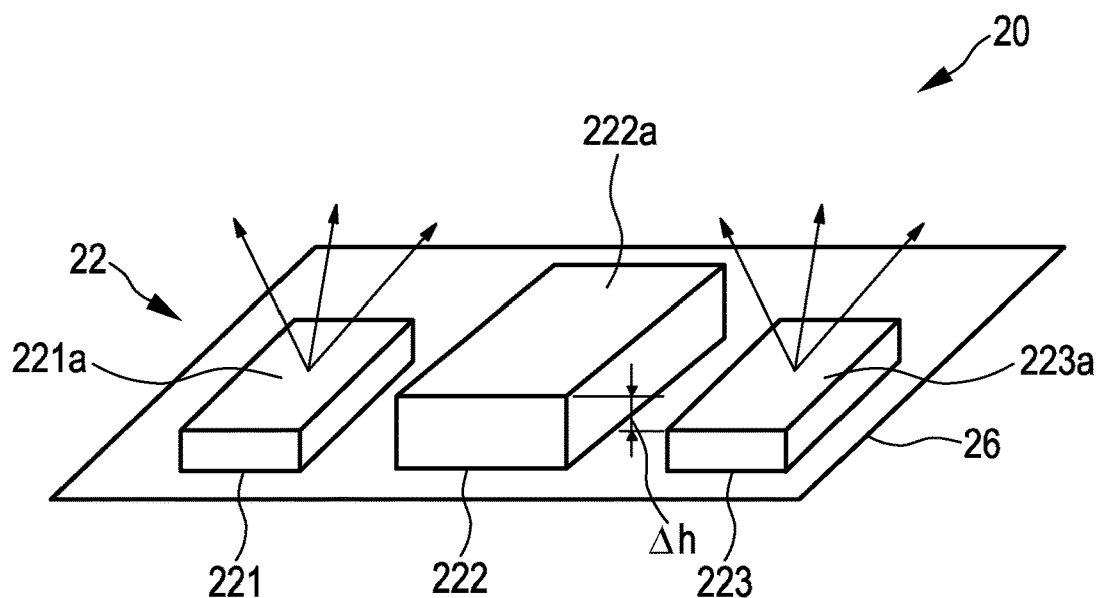
FIG. 2 shows a cross section through a first embodiment of a device according to the present invention.

FIG. 2 shows a cross section through a first embodiment of a device 20 for measuring a physiological parameter of a user carrying said device according to the present invention. Said device 20 comprises a sensor 22 comprising at least two (here three) sensor elements 221, 222, 223 for detecting a sensor signal, wherein said sensor is an optical sensor comprising two light emitting element 221, 223, in particular two LEDs, for emitting light to the user's skin and at least one light receiving element 222, in particular a photo detector, for receiving light reflected from the user's skin. Further, the device 20 comprises a case or housing (not shown; may generally be similar or identical as the case 14 shown in FIG. 1) and a carrier 26 carrying said sensor 22. This embodiment is however not preferred for use with an optical sensor because it allows light to go directly from the light emitting elements to the light receiving element without passing through the skin.

In this device 20 the distance between the carrier 26 and the top surface 221a, 223a of said light emitting elements 221, 223 is smaller than the distance between the carrier 26 and the top surface 222a said light receiving element 222, i.e. there is height distance Δh. This solution has the advantage that a large portion of the light from the light emitting elements 221, 223 is coupled directly (i.e. without intervention of a layer of air) towards the skin and further to the light receiving element 222. Furthermore, no light from the light emitting elements can enter the light receiving element 222 directly, without having passed through the skin.

Figure 3:
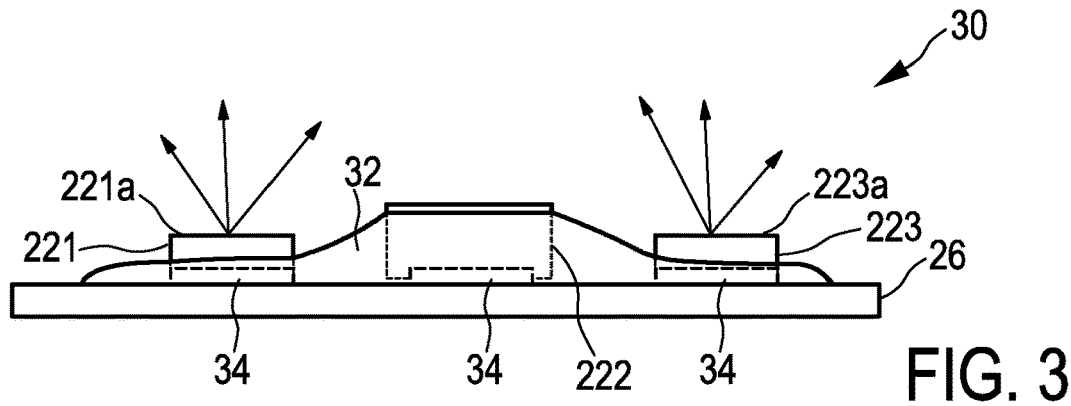
FIG. 3 shows a cross section through a second embodiment of a device according to the present invention.

For protection of the electrical components, the electrical contacts of the light emitting element(s) and the light receiving element(s) should preferably be covered with an insulator material, such as epoxy resin. It should, however, be avoided that the insulator material covers the light emitting element(s), because otherwise the skin cannot surround the light emitting elements giving the risk of air gaps and reduced grip of the skin on the light emitting elements. A generally possible embodiment of a device 30 according to the present invention, in which epoxy 32 is brought to protect the contacts of the light emitting elements 221, 223 without covering the top surface 221a, 223a of the light emitting elements 221, 223, is depicted in FIG. 3.

This embodiment can be further improved by practically bringing the epoxy 32 to cover the electrical contacts 34 of the components (i.e. the sensor elements 221, 222, 223), in such a way as to minimally interfere with a correct functioning of the sensor. Pouring of epoxy just like as shown in FIG. 3 is not optimal yet, since the epoxy may spill out. Creating additional structures to confine the epoxy is an option that allows high volume production.

Figure 4:
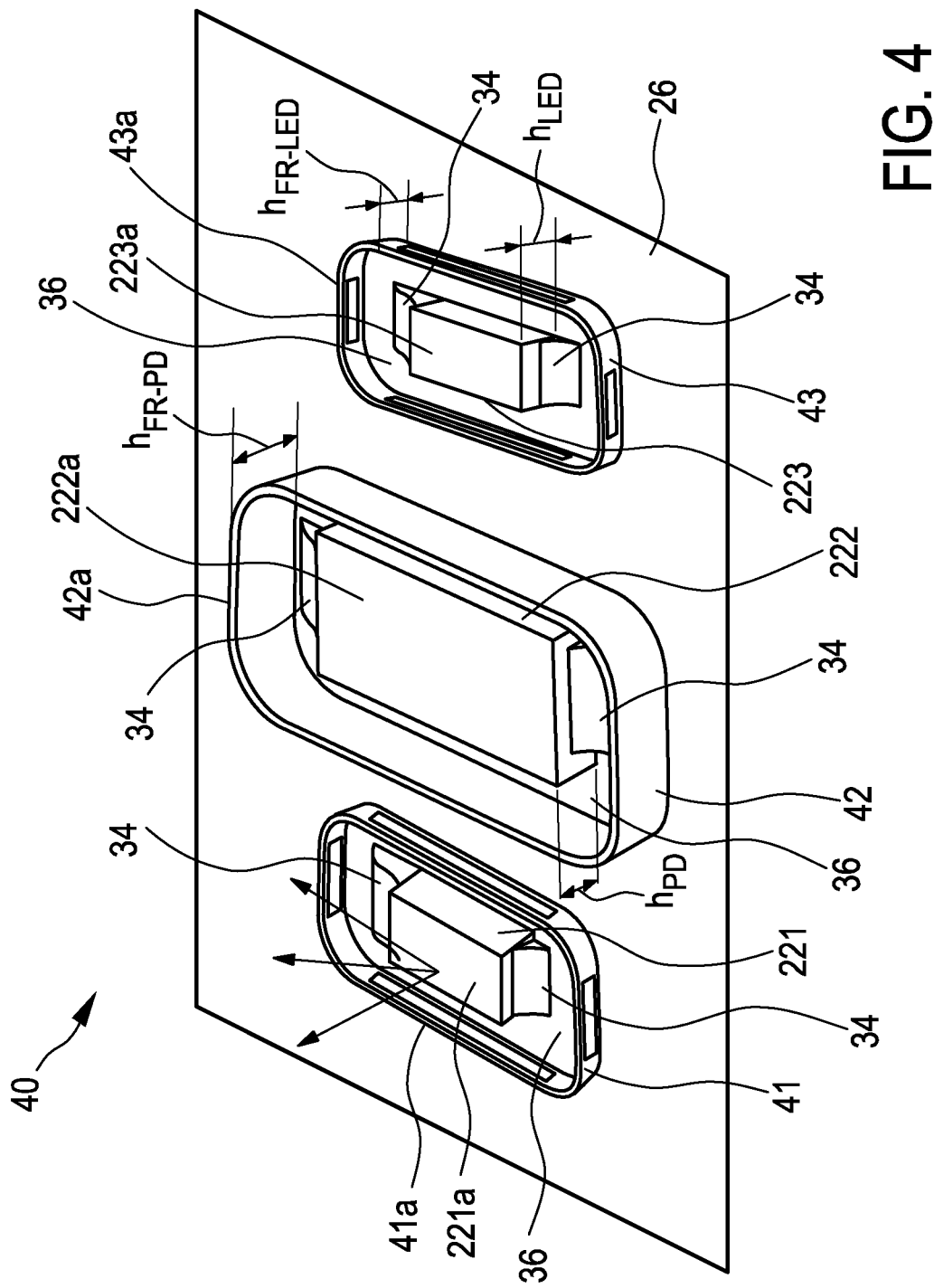
FIG. 4 shows a cross section through a third embodiment of a device according to the present invention.

FIG. 4 shows a further improved embodiment of a device 40 according to the present invention. In this embodiment structures are created in the device to confine the insulator material (which is not shown in FIG. 4). In particular, in this implementation that is suited for high-volume production frames 41, 42, 43 are formed around the sensor elements 221, 222, 223 that will confine the insulator material when it is poured over the electrical contacts 34 of the sensor elements in the space 36 between the frame and the optically active parts of the sensor elements.

In the embodiment shown in FIG. 4 every sensor element 221, 222, 223 is surrounded by an individual frame 41, 42, 43. In other embodiments some or all frames are combined with each other, or all sensor elements are surrounded by a common frame.

To further improve such a device so that it does not negatively affect the functioning of the device it has been found that the frames 41, 43 around the light emitting elements 221, 223 are preferably lower than the top surface 221a, 223a of the light emitting elements 221, 223. In other words, in such an improved implementation the light emitting elements 221, 223, in particular each light emitting element, is surrounded by a separate emitter frame 41, 43 having a height from the carrier 26 that is smaller than or equal to the distance between the carrier 26 and the top surface 221a, 223a of the respective light emitting element 221, 223 surrounded by said emitter frame 41, 43. This can be quantified in FIG. 4 by the relation $h_{FR-LED} < h_{LED}$. Preferably, the height difference between the top edge 41a, 43a of the emitter frames and the top surface 221a, 223a of the respective light emitting element 221, 223 surrounded by said emitter frame 41, 43 is in the range from 0.1 mm to 0.8 mm, in particular in the range from 0.2 mm to 0.5 mm.

Regarding the receiver frame 42 around the light receiving element 222 it is preferred that this is higher than the top surface 222a of the light receiving element 222. In other words, in such an improved implementation the receiver frames 42 has a height from the carrier 26 that is larger than the distance between the carrier 26 and the top surface 222a of the light receiving element 222 surrounded by said receiver frame 42. This can be quantified in FIG. 4 by the relation $h_{FR-PD} > h_{PD}$. Preferably, the height difference between the top edge 42a of the receiver frame 42 and the top surface 222a of the light receiving element 222 surrounded by said receiver frame 42 is in the range from 0 mm to 0.5 mm, in particular in the range from 0.1 mm to 0.2 mm.

It may occur for reasons of manufacturability that only one frame wall between the light receiving element and the light emitting element is present, e.g. in cases where the light receiving element and light emitting element are close. If that is the case the frame walls of both the frames of respectively the light receiving and light emitting elements coincide. This means that the frame wall of the light emitting element will be higher than the surface of the light emitting element itself, but only at the side where the light receiving element is situated. The remainder of the frame of the light emitting element will be lower than the surface of the element itself, in accordance with the above mentioned requirements.

The height of the top surface of the light emitting element(s) should be lower than the top edge 42a of frame 42 around the light receiving element. The height difference should be in the range from 0.1 to 1 mm, preferably in the range from 0.2 to 0.8 mm.

Figure 5:
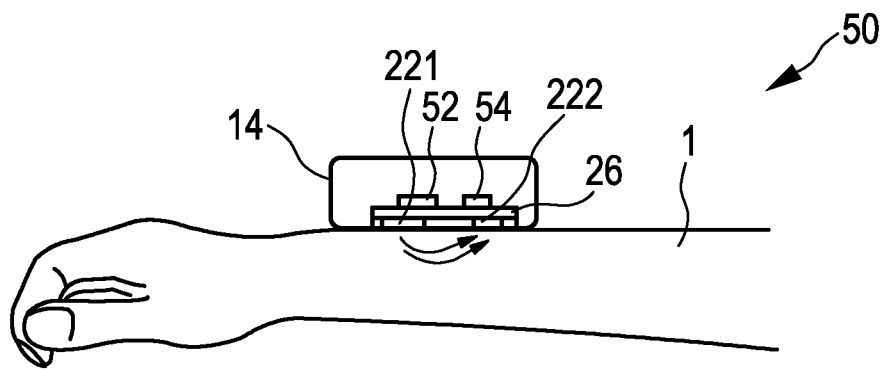
FIG. 5 shows a cross section through a fourth embodiment of a device according to the present invention.

As explained above, the insulator material will protect the electrical contacts 34 of the sensor elements. However, these electrical contacts 34 should further make contact with other elements, such as a driver, detection electronics, processor or power source, meaning that on the carrier 26 (which may be a PCB (Printed Circuit Board)) there are some "external" electrical connections to these additional electronics. FIG. 5 shows a cross section through a fourth embodiment of a device 50 according to the present invention. Said device 50 comprises such additional electronics, such as a processor 52 and a driver 54. The external electrical connections are not placed on the same surface of the carrier 26 as the sensor elements 221, 222. Otherwise the parts to which they are connected would impede good contact between the skin and the sensor elements. For instance, the external electrical connections can be placed on the side surfaces of the carrier 26.

As mentioned above different kinds of sensors can be used in a device according to the present invention. For instance, in an embodiment said sensor 22 is an electrical sensor comprising two skin conductance electrodes (e.g. the sensor elements 221, 222 shown in FIG. 2) for contacting the user's skin and measuring conductivity the user's skin. Still further, two or more of sensor can generally be used in such a device, and also the number of sensor elements is not essential for the present invention.

Figure 6:
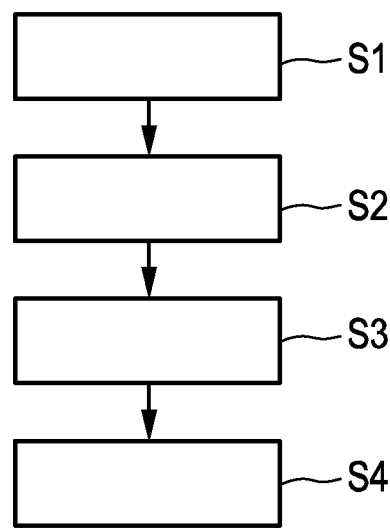
FIG. 6 shows a flow chart of a method of manufacturing a device according to the present invention.

A flow chart of a method of manufacturing a device for measuring a physiological parameter as proposed herein is depicted in FIG. 6. In a first step S1 the sensor 22 comprising at least two sensor elements 221, 222 for detecting a sensor signal is arranged on the carrier 26. In a second step S2 electrical contacts of said sensor elements are formed on, into or through said carrier 26. In a third step S3 one or more frames 41, 42 are formed on said carrier 26 around said sensor 22 and/or said individual sensor elements 221, 222. In a fourth step S4 insulator material 32 is filled between said one or more frames 41, 42 and the sensor 22 and/or the sensor elements 221, 222 surrounded by the respective frame 41, 42 without covering the top surface 221a, 222a of the respective sensor element 221, 222 facing away from the carrier 26.

In summary, according to the present invention a way of achieving a protection of the electrical contacts without having a negative effect on the performance of the device is proposed. For this purpose frame(s) around sensor elements is (are) used, made in such a way as to preserve the performance of the sensor. For instance, at least one of these frames helps to prevent shifting of the sensor across the skin; moreover, at least one of these frames may serve to prevent direct emitted light from entering the light receiving element. Preferably, the height of the frame around the light emitting element(s) should be smaller than the height of the surface of the light emitting element(s), with the possible exception of the side facing the light receiving element. In addition, the frame around the light receiving element(s) may be higher than the surface of the light receiving element(s).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A device for measuring a physiological parameter of a user carrying the device, the device comprising:
   an optical sensor comprising sensor elements,
      wherein the sensor elements comprise:
         at least one light emitting element,
            wherein the at least one light emitting element is configured to emit light to the user's skin; and
         at least one light receiving element,
            wherein the at least one light receiving element is configured to receive light reflected from the user's skin;
   a carrier configured to carry the optical sensor,
      wherein the optical sensor is located on a surface of the carrier,
      wherein electrical contacts of the sensor elements lead on, into, and/or through the carrier,
      wherein the receiver frame is located on the surface of the carrier,
      wherein the receiver frame separates the at least one light receiving element from the at least one light emitting element,
   wherein the receiver frame has a height from a surface of the carrier of that is larger than a distance between the surface of the carrier and a top surface of the at least one light receiving element;
   at least one emitter frame,
      wherein the at least one emitter frame is located on the surface of the carrier, and
      wherein the at least one emitter frame is formed around the at least one light emitting element; and
   an insulator material,
      wherein the insulator material is filled between the at least one emitter frame and the at least one light emitting element, wherein the insulator material is filled up to a height that is equal to or smaller than the a distance between the carrier and a top surface of the at least one light emitting element, wherein the at least one emitter frame has a height from the carrier that is smaller than the distance between the carrier and the top surface of the light emitting element, and wherein the at least one emitter frame has a height greater than zero.

2. The device as claimed in claim 1, wherein a height difference between a top edge of the receiver frame and the top surface of the at least one light receiving element is in a range from 0.1 mm to 0.5 mm.

3. The device as claimed in claim 1, wherein a height difference between a top edge of the at least one emitter frame and the top surface of the at least one light emitting element is in a range from 0.1 mm to 0.8 mm.

4. The device as claimed in claim 1, further comprising an electrical sensor comprising two skin conductance electrodes,
wherein the two skin conductance electrodes are configured to contact the user's skin, and
wherein the two skin conductance electrodes are configured to measure conductivity of the user's skin.

5. The device as claimed in claim 1, further comprising a processor configured to process a sensor signal detected by the optical sensor.

6. The device as claimed in claim 5, wherein the processor is arranged on the carrier on a different surface than the optical sensor.

7. The device as claimed in claim 1, wherein the insulator material is epoxy resin.

8. The device as claimed in claim 1, further comprising a fixation element configured to fix the device to the user's skin.

9. The device as claimed in claim 8, wherein the fixation element is one of a wristband, an adhesive strip, a band aid, and a strap.

10. The device as claimed in claim 1, wherein the at least one light emitting element is a light emitting diode.

11. The device as claimed in claim 1, wherein the at least one light receiving element is a photo-detector.

12. The device as claimed in claim 1, wherein a height difference between a top edge of the receiver frame and the top surface of the at least one light receiving element is in a range from 0.1 mm to 0.2 mm.

13. The device as claimed in claim 1, wherein a height difference between a top edge of the at least one emitter frame and the top surface of the at least one light emitting element is in a range from 0.2 mm to 0.5 mm.

14. A method of manufacturing a device configured to measure a physiological parameter of a user carrying the device, the method comprising:

arranging an optical sensor on a surface of a carrier,
wherein the optical sensor comprising sensor elements,
wherein the sensor elements comprise:
at least one light emitting element,
wherein the at least one light emitting element is configured to emit light to the user's skin, and
at least one light receiving element,
wherein the at least one light receiving element is configured to receive light reflected from the user's skin;
wherein each of the sensor elements has a top surface facing away from the carrier;
forming electrical contacts of the sensor elements on, into, and/or through the carrier,
forming at least one emitter frame on the surface of the carrier around the at least one light emitting element; and
filling insulator material between the at least one emitter frame and the at least one light emitting element,
wherein the insulator material is filled up to a height that is equal to or smaller than a distance between the carrier and a top surface of the at least one light emitting element, and
wherein the at least one emitter frame has a height from the carrier that is smaller than the distance between the carrier and the top surface of the light emitting element, and
wherein the at least one emitter frame has a height greater than zero,
wherein the receiver frame separates the at least one light receiving element from the at least one light emitting element,
wherein the receiver frame has a height from the surface of the carrier that is larger than a distance between the surface of the carrier and a top surface of the at least one light receiving element.

15. The method as claimed in claim 14, wherein a height difference between a top edge of the at least one emitter frame and the top surface of the at least one light emitting element is in a range from 0.1 mm to 0.8 mm.

16. The method as claimed in claim 14, wherein a height difference between a top edge of the receiver frame and the top surface of the at least one light receiving element is in a range from 0.1 mm to 0.5 mm.

17. The method as claimed in claim 14, wherein the at least one light emitting element is an LED.

18. The method as claimed in claim 14, wherein the at least one light receiving element is a photo-detector.

19. The method as claimed in claim 14, comprising arranging a processor on the carrier, wherein the processor is configured to process a sensor signal detected by the optical sensor.

20. The method as claimed in claim 19, wherein the processor is arranged on the carrier on a different surface than the optical sensor.

* * * * *